US008048627B2

(12) United States Patent
Dressman et al.

(10) Patent No.: US 8,048,627 B2
(45) Date of Patent: Nov. 1, 2011

(54) METHOD AND COMPOSITIONS FOR DETECTION AND ENUMERATION OF GENETIC VARIATIONS

(75) Inventors: Devin Dressman, Baltimore, MD (US); Hai Yan, Chapel Hill, NC (US); Kenneth W Kinzler, Baltimore, MD (US); Bert Vogelstein, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1137 days.

(21) Appl. No.: 10/562,840

(22) PCT Filed: Jun. 9, 2004

(86) PCT No.: PCT/US2004/015587
§ 371 (c)(1),
(2), (4) Date: Jun. 22, 2006

(87) PCT Pub. No.: WO2005/010145
PCT Pub. Date: Feb. 3, 2005

(65) Prior Publication Data
US 2007/0065823 A1    Mar. 22, 2007

Related U.S. Application Data

(60) Provisional application No. 60/485,301, filed on Jul. 5, 2003, provisional application No. 60/525,859, filed on Dec. 1, 2003.

(51) Int. Cl.
*C12Q 1/68* (2006.01)
*C12P 19/34* (2006.01)
*C07H 21/02* (2006.01)

(52) U.S. Cl. .................. 435/6.12; 536/23.1; 435/91.2

(58) Field of Classification Search .............. None
See application file for complete search history.

(56) References Cited

U.S. PATENT DOCUMENTS
4,801,529 A    1/1989  Perlman et al. ................. 435/5
(Continued)

FOREIGN PATENT DOCUMENTS
CA    2 513 535    8/2004
(Continued)

OTHER PUBLICATIONS

Andreadnis et al. Use of immobilized PCR primers to generate covalently immobilized DNAs for in vitro transcription/translation reactions. Nucleic Acids Research 28(2):e5(i-viii), 2000.*

(Continued)

*Primary Examiner* — Samuel Woolwine
(74) *Attorney, Agent, or Firm* — Banner & Witcoff, Ltd.

(57) ABSTRACT

Many areas of biomedical research depend on the analysis of uncommon variations in individual genes or transcripts. Here we describe a method that can quantify such variation at a scale and ease heretofore unattainable. Each DNA molecule in a collection of such molecules is converted into a single particle to which thousands of copies of DNA identical in sequence to the original are bound. This population of beads then corresponds to a one-to-one representation of the starting DNA molecules. Variation within the original population of DNA molecules can then be simply assessed by counting fluorescently-labeled particles via flow cytometry. Millions of individual DNA molecules can be assessed in this fashion with standard laboratory equipment. Moreover, specific variants can be isolated by flow sorting and employed for further experimentation. This approach can be used for the identification and quantification of rare mutations as well as to study variations in gene sequences or transcripts in specific populations or tissues.

21 Claims, 8 Drawing Sheets

U.S. PATENT DOCUMENTS

| | | | |
|---|---|---|---|
| 5,405,746 A | 4/1995 | Uhlen | |
| 5,503,851 A | 4/1996 | Hank et al. | 424/489 |
| 5,546,792 A * | 8/1996 | Becker | 73/64.53 |
| 5,750,341 A * | 5/1998 | Macevicz | 435/6 |
| 5,989,892 A | 11/1999 | Nishimaki et al. | 435/252.1 |
| 6,023,540 A | 2/2000 | Walt et al. | 385/12 |
| 6,184,012 B1 | 2/2001 | Neri et al. | 435/188 |
| 6,258,858 B1 | 7/2001 | Nakajima et al. | 516/73 |
| 6,266,459 B1 | 7/2001 | Walt et al. | 385/12 |
| 6,303,309 B1 | 10/2001 | Jurinke et al. | 435/6 |
| 6,306,597 B1 * | 10/2001 | Macevicz | 435/6 |
| 6,310,354 B1 | 10/2001 | Hanninen et al. | 250/458.1 |
| 6,355,431 B1 | 3/2002 | Chee et al. | |
| 6,403,037 B1 * | 6/2002 | Chang et al. | 422/68.1 |
| 6,440,706 B1 | 8/2002 | Vogelstein et al. | |
| 6,489,103 B1 | 12/2002 | Griffiths et al. | 435/6 |
| 6,808,882 B2 | 10/2004 | Griffiths et al. | |
| 7,323,305 B2 * | 1/2008 | Leamon et al. | 435/6 |
| 2001/0020011 A1 | 9/2001 | Mathiowitz et al. | 514/44 |
| 2002/0001801 A1 | 1/2002 | Fan et al. | |
| 2002/0022038 A1 | 2/2002 | Griffiths et al. | 435/6 |
| 2002/0102590 A1 * | 8/2002 | Taing et al. | 435/6 |
| 2002/0119459 A1 | 8/2002 | Griffiths | 435/6 |
| 2002/0155080 A1 | 10/2002 | Glenn et al. | 424/70.5 |
| 2003/0064400 A1 * | 4/2003 | Williams | 435/6 |
| 2003/0065144 A1 * | 4/2003 | Bamber et al. | 530/350 |
| 2003/0105039 A1 * | 6/2003 | Zarling et al. | 514/44 |
| 2003/0124586 A1 | 7/2003 | Griffiths et al. | 435/6 |
| 2003/0129640 A1 | 7/2003 | Sasaki et al. | |
| 2004/0005594 A1 | 1/2004 | Holliger et al. | 435/6 |
| 2004/0053254 A1 | 3/2004 | Wangh et al. | 435/6 |
| 2004/0185484 A1 | 9/2004 | Costa et al. | |
| 2004/0253731 A1 | 12/2004 | Holliger et al. | 435/458 |
| 2005/0037392 A1 | 2/2005 | Griffiths et al. | 435/6 |
| 2005/0042648 A1 | 2/2005 | Griffiths et al. | 435/6 |
| 2005/0064460 A1 | 3/2005 | Holliger et al. | 435/6 |
| 2005/0069920 A1 | 3/2005 | Griffiths et al. | 435/6 |
| 2005/0164239 A1 | 7/2005 | Griffiths et al. | 435/6 |
| 2006/0234221 A1 * | 10/2006 | Cohen et al. | 435/6 |

FOREIGN PATENT DOCUMENTS

| | | |
|---|---|---|
| DE | 196 46 372 | 6/1997 |
| DE | 196 46 372 C1 | 6/1997 |
| EP | 0 392 546 | 4/1990 |
| EP | 0392546 A2 | 10/1990 |
| EP | 0 579 347 | 1/1994 |
| EP | 1 482 036 | 1/2004 |
| EP | 1 482 036 A2 | 1/2004 |
| EP | 1 522 581 | 4/2005 |
| EP | 1 522 582 | 4/2005 |
| WO | WO 8911546 A1 * | 11/1989 |
| WO | 91/05058 | 4/1991 |
| WO | WO 91/05058 | 4/1991 |
| WO | 93/03151 | 2/1993 |
| WO | WO 93/03151 A | 2/1993 |
| WO | 93/08278 | 4/1993 |
| WO | WO 93/08278 A | 4/1993 |
| WO | 94/16332 | 7/1994 |
| WO | WO 94/16332 | 7/1994 |
| WO | 94/23738 | 10/1994 |
| WO | 94/24314 | 10/1994 |
| WO | WO 94/23738 A | 10/1994 |
| WO | WO 94/24314 | 10/1994 |
| WO | 94/26766 | 11/1994 |
| WO | WO 94/26766 | 11/1994 |
| WO | 95/11922 | 5/1995 |
| WO | WO 95/11922 | 5/1995 |
| WO | 95/24929 | 9/1995 |
| WO | WO 95/24929 A | 9/1995 |
| WO | 96/34112 | 10/1996 |
| WO | WO 96/34112 A | 10/1996 |
| WO | 96/40723 | 12/1996 |
| WO | WO 96/40723 | 12/1996 |
| WO | 97/40141 | 10/1997 |
| WO | WO 97/40141 | 10/1997 |
| WO | 97/47763 | 12/1997 |
| WO | WO 97/47763 | 12/1997 |
| WO | 98/13502 | 4/1998 |
| WO | WO 98/13502 | 4/1998 |
| WO | 98/23733 | 6/1998 |
| WO | WO 98/23733 | 6/1998 |
| WO | 98/31700 | 7/1998 |
| WO | WO 98/31700 A | 7/1998 |
| WO | 98/34120 | 8/1998 |
| WO | 98/37186 | 8/1998 |
| WO | WO 98/34120 | 8/1998 |
| WO | WO 98/37186 | 8/1998 |
| WO | 98/41869 | 9/1998 |
| WO | WO 98/41869 A | 9/1998 |
| WO | 99/02671 | 1/1999 |
| WO | WO 99/02671 | 1/1999 |
| WO | 00/04139 | 1/2000 |
| WO | WO 00/04139 | 1/2000 |
| WO | 00/40712 | 7/2000 |
| WO | WO 00/40712 | 7/2000 |
| WO | WO 00/40712 A1 | 7/2000 |
| WO | 01/18244 | 3/2001 |
| WO | WO 01/18244 | 3/2001 |
| WO | 02/22869 | 3/2002 |
| WO | WO 02/22869 | 3/2002 |
| WO | WO 02/22869 A2 | 3/2002 |
| WO | 02/103363 | 12/2002 |
| WO | WO 02/103363 | 12/2002 |
| WO | 03/044187 | 5/2003 |
| WO | WO 03/044187 | 5/2003 |
| WO | WO 03/044187 A2 | 5/2003 |
| WO | WO 03/106678 A1 | 12/2003 |
| WO | 2004/069849 | 8/2004 |
| WO | WO 2004/069849 A2 | 8/2004 |
| WO | 2004/083443 | 9/2004 |
| WO | WO 2004/083443 A1 | 9/2004 |

OTHER PUBLICATIONS

Nikiforov et al. Genetic Bit Analysis: a solid phase method for typing single nucleotide polymorphisms. Nucleic Acids Research 22(20):4167-4175 (1994).*

Kricka, L. Stains, labels and detection strategies for nucleic acids assays. Annals of Clinical Biochemistry 39:114-129, Mar. 2002.*

A. Sepp, "Microbead Display by In Vitro Compartmentalisation: Selection for Binding Using Flow Cytometry," FEBS Lett. Dec. 18, 2002;532(3):455-8.

Andrew D. Griffiths et al., "Directed Evolution of an Extremely Fast Phosphotriesterase by in vitro Comparmentalization," The EMBO Journal, 2003, vol. 22, No. 1, pp. 24-35.

Farid J. Ghadessy, "Directed Evolution of Polymerase Functio by Compartmentalized Self-Replication," PNAS, Apr. 10, 2001, vol. 98, No. 8, pp. 4552-4557.

Bert Vogelstein et al., "Digital PCR," Proc. Natl., Acad. Sci., Aug. 1999, vol. 96, pp. 9236-9241.

Michihiko Nakano et al., "Single-Molecule PCR Using Water-In-Oil Emulsion," Journal of Biotechnology, 102 (2003) 117-124.

Thomas Oberholzer et al., "Polymerase Chain Reaction in Liposomes," Chemistry & Biology, Oct. 1995, 2:677-682.

Shinji Katsura, "Indirect Micromanipulation of Single Molecules in Water-in-Oil Emulsion," Electrophoresis 2001, 22, 289-293.

Dressman et al., "Transforming Single DNA Molecules Into Fluorescent Magnetic Particles for Detection and Enumeration of Genetic Variations," Jul. 22, 2003, pp. 8817-8822, PNAS www.pnas.org/cgi/doi/10.1073/pnas.1133470100.

Ghadessy et al., "Directed Evolution of Polymerase Function By Compartmentalized Self-Replication," Apr. 10, 2001; pp. 4552-4557, PNAS, vol. 98, No. 8.

U.S. Appl. No. 60/443,471, filed Jan. 29, 2003, Weiner et al.
U.S. Appl. No. 60/476,504, filed Jun. 6, 2003, Berka et al.
U.S. Appl. No. 60/465,071, filed Apr. 23, 2003, Lohman.
U.S. Appl. No. 60/497,985, filed Aug. 25, 2003, Leamon et al.
U.S. Appl. No. 60/476,313, filed Jun. 6, 2003, Chen et al.
U.S. Appl. No. 60/476,602, filed Jun. 6, 2003, Costa et al.

Ghosh et al: "Covalent Attachment of Oligonucleotides to Solid Supports", Nucleic Acids Research. 1987, vol. 15, No. 13, pp. 5353-5372.

M.J. Brisco et al., "Detection and Quantitation of Neoplastic Cells in Acute Lymphoblastic Leukaemia, by Use of the Polymerase Chain Reaction," British Journal of Haematology, 1991, 79, 211-217.

M. J. Brisco et al., "Outcome Prediction in Childhood Acute Lymphoblastic Leukaemia by Molecular Quantification of Residual Disease at the End of Induction," The Lancet, Jan. 22, 1994, vol. 343, pp. 196-200.

P. J. Sykes et al, "Quantitation of Targets for PCR by Use of Limiting Dilution," BioTechniques, 1992, vol. 13, No. 3, pp. 444-449.

Ghosh et al. "Covalent Attachment of Oligonucleotides to Solid Supports", Nucleic Acids Research. 1987, vol. 15, No. 13, pp. 5353-5372.

Yamaguchi et al. "Indirect Micromanipulation of Single Molecules in Water-In-Oil Emulsion." Electrophoresis. Jan. 2001; 22(2): 289-93. (abstract only).

Vogelstein et al. "Digital PCR" Proc. Natl. Acad. Sci. USA vol. 96, pp. 9236-9241, Aug. 1999.

Supplementary European Search Report dated Apr. 15, 2010 in European Application No. 04752581.1.

U.S.P.T.O. Office Action in co-pending U.S. Appl. No. 12/361,690 dated Sep. 17, 2009.

U.S.P.T.O. Office Action in co-pending U.S. Appl. No. 12/361,690 dated Jun. 15, 2010.

* cited by examiner

Fig. 8.     Oligonucleotides

| Locus | Oligonucleotide* | Modification | Use** |
|---|---|---|---|
| MID42 | 5'-tactatgtatttatacgttaagacctctatgaatgaatgta | 5' Dual biotin | Bound to Beads |
| MID42 | 5'-cgttaagacctctatgaatgaatgta | none | Forward Primer for PCR |
| MID42 | 5'-gaaaggtaagtacagggaaagg | none | Reverse Primer for PCR |
| MID42 | 5'-cacgcagattgaattaaacAGTTagttacaaagacacgtg | 5' 6-FAM | Hybridization probe for L allele |
| MID42 | 5'-cacgcagattgaattaaacagttacaaagacacgtg | 5' Biotin | Hybridization probe for S allele |
| Calpain-10 | 5'-aggtcccagagggtggaaggagccaggacgcacccccactgctgctg | 5' Dual Biotin | Bound to Beads |
| Calpain-10 | 5'-aggtcccagagggtggaag | none | Forward Primer for PCR |
| Calpain-10 | 5'-ttgcgatggtcactgtgaag | none | Reverse Primer for PCR |
| Calpain-10 | 5'-cacggtaggtgctTgcaggcagcgtg | 5' 6-FAM | Hybridization probe for A allele |
| Calpain-10 | 5'-cacggtaggtgccCgcaggcagcgtg | 5' Biotin | Hybridization probe for G allele |
| KRAS2 | 5'-ttcgtccacaaaatgattctgaattagctgtatcgtcaagg | 5' Dual Biotin | Bound to Beads |
| KRAS2 | 5'-agaatggtcctgcaccagtaa | none | Reverse Primer for PCR |
| KRAS2 | 5'-catgttctaatatagtcacattttca | none | Forward Primer for PCR |
| KRAS2 | 5'-cacgggagctGGTGGCgtagcgtg | 5' 6-FAM | Hybridization probe for wt allele |
| KRAS2 | 5'-ccacgggagctgatggcgtagcgtgg | 5' Biotin | Hybridization probe for mutant allele |

*Bases in upper case represent allelic differences.   SEQ ID NOS: 3-17, respectively.
**Hybridization probes each contained 4 bases at their 5' and 3' ends to form hairpins, as explained in the text.

SEQUENCE LISTING

```
<160> NUMBER OF SEQ ID NOS: 17

<210> SEQ ID NO 1
<211> LENGTH: 20
<212> TYPE: DNA
<213> ORGANISM: Homo sapiens

<400> SEQUENCE: 1
ctttgtaact aactgtttaa                                                      20

<210> SEQ ID NO 2
<211> LENGTH: 16
<212> TYPE: DNA
<213> ORGANISM: Homo sapiens

<400> SEQUENCE: 2
ctttgtaact gtttaa                                                          16

<210> SEQ ID NO 3
<211> LENGTH: 40
<212> TYPE: DNA
<213> ORGANISM: Artificial Sequence
<220> FEATURE:
<223> OTHER INFORMATION: probe

<400> SEQUENCE: 3
tactatgtat ttatagttaa gacctctatg aatgaatgta                                40

<210> SEQ ID NO 4
<211> LENGTH: 26
<212> TYPE: DNA
<213> ORGANISM: Artificial Sequence
<220> FEATURE:
<223> OTHER INFORMATION: probe

<400> SEQUENCE: 4
```
cgttaagacc tctatgaatg aatgta                                        26

<210> SEQ ID NO 5
<211> LENGTH: 22
<212> TYPE: DNA
<213> ORGANISM: Artificial Sequence
<220> FEATURE:
<223> OTHER INFORMATION: probe

<400> SEQUENCE: 5
gaaaggtaag tacagggaaa gg                                            22

<210> SEQ ID NO 6
<211> LENGTH: 40
<212> TYPE: DNA
<213> ORGANISM: Artificial Sequence
<220> FEATURE:
<223> OTHER INFORMATION: probe

<400> SEQUENCE: 6
cacgcagatt gaattaaaca gttagttaca aagacacgtg                         40

<210> SEQ ID NO 7
<211> LENGTH: 36
<212> TYPE: DNA
<213> ORGANISM: Artificial Sequence
<220> FEATURE:
<223> OTHER INFORMATION: probe

<400> SEQUENCE: 7
cacgcagatt gaattaaaca gttacaaaga cacgtg                             36

<210> SEQ ID NO 8
<211> LENGTH: 47
<212> TYPE: DNA
<213> ORGANISM: Artificial Sequence
<220> FEATURE:
<223> OTHER INFORMATION: probe

<400> SEQUENCE: 8
aggtcccaga gggtggaagg agccaggacg caccccact gctgctg                  47

<210> SEQ ID NO 9
<211> LENGTH: 19
<212> TYPE: DNA
<213> ORGANISM: Artificial Sequence
<220> FEATURE:
<223> OTHER INFORMATION: probe

<400> SEQUENCE: 9
aggtcccaga gggtggaag                                                19

<210> SEQ ID NO 10
<211> LENGTH: 20
<212> TYPE: DNA
<213> ORGANISM: Artificial Sequence
<220> FEATURE:
<223> OTHER INFORMATION: probe

<400> SEQUENCE: 10
ttgcgatggt cactgtgaag                                               20

<210> SEQ ID NO 11
<211> LENGTH: 26
<212> TYPE: DNA
<213> ORGANISM: Artificial Sequence

```
<220> FEATURE:
<223> OTHER INFORMATION: probe

<400> SEQUENCE: 11
cacggtaggt gcttgcaggc agcgtg                                          26

<210> SEQ ID NO 12
<211> LENGTH: 26
<212> TYPE: DNA
<213> ORGANISM: Artificial Sequence
<220> FEATURE:
<223> OTHER INFORMATION: probe

<400> SEQUENCE: 12
cacggtaggt gcccgcaggc agcgtg                                          26

<210> SEQ ID NO 13
<211> LENGTH: 41
<212> TYPE: DNA
<213> ORGANISM: Artificial Sequence
<220> FEATURE:
<223> OTHER INFORMATION: probe

<400> SEQUENCE: 13
ttcgtccaca aaatgattct gaattagctg tatcgtcaag g                         41

<210> SEQ ID NO 14
<211> LENGTH: 21
<212> TYPE: DNA
<213> ORGANISM: Artificial Sequence
<220> FEATURE:
<223> OTHER INFORMATION: probe

<400> SEQUENCE: 14
agaatggtcc tgcaccagta a                                               21

<210> SEQ ID NO 15
<211> LENGTH: 26
<212> TYPE: DNA
<213> ORGANISM: Artificial Sequence
<220> FEATURE:
<223> OTHER INFORMATION: probe

<400> SEQUENCE: 15
catgttctaa tatagtcaca ttttca                                          26

<210> SEQ ID NO 16
<211> LENGTH: 24
<212> TYPE: DNA
<213> ORGANISM: Artificial Sequence
<220> FEATURE:
<223> OTHER INFORMATION: probe

<400> SEQUENCE: 16
cacgggagct ggtggcgtag cgtg                                            24

<210> SEQ ID NO 17
<211> LENGTH: 26
<212> TYPE: DNA
```

```
<213> ORGANISM: Artificial Sequence
<220> FEATURE:
<223> OTHER INFORMATION: probe

<400> SEQUENCE: 17
ccacgggagc tgatggcgta gcgtgg                                           26
```

US 8,048,627 B2

METHOD AND COMPOSITIONS FOR DETECTION AND ENUMERATION OF GENETIC VARIATIONS

This application is a national stage application of co-pending PCT application PCT/US2004/015587 filed Jun. 9, 2004, which was published in English under PCT Article 21(2) on Feb. 3, 2005, which claims the benefit of application Ser. No. 60/485,301, filed Jul. 5, 2003 and 60/525,859, filed Dec. 1, 2003, the contents of both of which are expressly incorporated herein.

The invention disclosed herein was made using funds from the National Institutes of Health grants CA 43460, CA 57345, and CA62924. The United States government therefore retains certain rights in the invention.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The invention relates to the field of genetic analysis. In particular, it relates to methods and compositions for analyzing variations in individual genes or transcripts and separating variants.

BACKGROUND OF THE INVENTION

The study of DNA sequence variation is essential for many areas of research. The study of germ-line variations is essential for assessing the role of inheritance in normal and abnormal physiologic states (1). Other variations, developed somatically, are responsible for neoplasia (2). The identification of such mutations in urine, sputum, and stool can therefore be used for the detection of presymptomatic cancers (3-5). Similarly, the detection of somatic mutations in lymph nodes, blood, or bone marrow can provide data about the stage of disease, prognosis, and appropriateness of various therapies (5). Somatic mutations in non-neoplastic cells also occur and appear to accumulate as humans age or are exposed to environmental hazards (6). Such mutations occur in only a small fraction of the cells in a tissue, thereby complicating their analysis.

Central to the investigation of many of these issues is the detection and quantification of sequence variants within a population of DNA molecules. The number of molecules in each such collection is finite and therefore countable.

Consider, for example, a collection of red and green balls. Counting these balls is simple in principle but subject to basic probability theory. If there is only one red ball for every 500 green balls, then it is necessary to count several thousand balls to get an accurate estimate of the proportion of red balls. If it is difficult to count enough balls to make a reliable estimate, one can elute the paint off all the balls and measure the color of the resultant paint mix.

In analogous fashion, small numbers of DNA molecules that vary by subtle changes (single base pair substitutions or small deletions or insertions) can be directly counted by amplifying individual DNA molecules (single molecule PCR) (7-12). Such digital techniques have been shown to be extremely useful for measuring variation in genes or their transcripts. But digital technologies have so far been limited to counting tens to thousands of molecules, either in the wells of microtiter plates, on microscope slides, or after electrophoresis of individual PCR products. Analog techniques, analogous to the elution of paint from the balls described above, are generally easier to implement and can assess millions of molecules simultaneously (13). However, their accuracy and sensitivity is limited by instrumental and experimental noise. There is a continuing need in the art for methods which are accurate and sensitive for measuring variation in genes or their transcripts.

BRIEF SUMMARY OF THE INVENTION

In a first embodiment of the invention a composition is provided. The composition comprises a plurality of beads. Each of the plurality of beads comprises a plurality of bound polynucleotides. The polynucleotides in the composition are heterogeneous; however, on at least 1% of said beads the plurality of bound polynucleotides is homogeneous.

In a second embodiment of the invention a liquid composition is provided. The liquid composition comprises a plurality of microemulsions forming aqueous compartments. At least a portion of said aqueous compartments comprise a bead, a polynucleotide template, and oligonucleotide primers for amplifying the template. At least a portion of the oligonucleotide primers is bound to the bead.

A third embodiment of the invention provides a method for analyzing nucleotide sequence variations. Microemulsions comprising one or more species of analyte DNA molecules are formed. The analyte DNA molecules in the microemulsions are amplified in the presence of reagent beads which are bound to a plurality of molecules of a primer for amplifying the analyte DNA molecules. Product beads are formed that are bound to a plurality of copies of a single species of analyte DNA molecule. The product beads are separated from analyte DNA molecules which are not bound to product beads. A sequence feature of the single species of analyte DNA molecule that is bound to the product beads is determined.

A fourth embodiment of the invention is a probe for use in hybridization to a polynucleotide that is bound to a solid support. The probe comprises an oligonucleotide with a stem-loop structure. At one of the 5' or 3' ends there is a photoluminescent dye. The oligonucleotide does not comprise a quenching agent at the opposite 5' or 3' end.

A fifth embodiment of the invention is a pair of molecular probes. The first and second probes each comprise an oligonucleotide with a stem-loop structure having a first photoluminescent dye at one of the 5' or 3' ends, and not comprising a quenching agent at the opposite 5' or 3' end. The first oligonucleotide hybridizes to a wild-type selected genetic sequence better than to a mutant selected genetic sequence and the second oligonucleotide hybridizes to the mutant selected genetic sequence better than to the wild-type selected genetic sequence. The first and the second photoluminescent dyes are distinct.

In a sixth embodiment of the invention a method is provided for isolating nucleotide sequence variants. Microemulsions comprising one or more species of analyte DNA molecules are formed. Analyte DNA molecules in the microemulsions are amplified in the presence of reagent beads. The reagent beads are bound to a plurality of molecules of a primer for amplifying the analyte DNA molecules. Product beads are formed which are bound to a plurality of copies of one species of analyte DNA molecule. The product beads are separated from analyte DNA molecules which are not bound to product beads. The product beads which are bound to a plurality of copies of a first species of analyte DNA molecule are isolated from product beads which are bound to a plurality of copies of a second species of analyte DNA molecule.

These and other embodiments of the invention, which will be apparent from the entire description of the invention, provide the art with the ability to quantify genetic variations at a scale and ease heretofore unattainable.

BRIEF DESCRIPTION OF THE DRAWINGS

(FIG. 3A) Forward scatter (FSC) and side scatter (SSC) of all beads show that ~80% of the total beads are singlets, with most of the remaining beads aggregated as doublets. The "noise" is instrumental and is observed with blank samples containing no beads. The instrument output was gated so that only singlets were analyzed for fluorescence analysis. The patterns observed from an individual homozygous for the L allele (FIG. 3C), homozygous for the S allele (FIG. 3B), and heterozygous for L and S (FIG. 3D) are shown. The regions containing beads hybridizing to the L and S allele probes are labeled green and red, respectively. The region containing beads that did not hybridize to any probe is black and the region containing beads that hybridized to both probes is blue. The blue beads arose from aqueous compartments in which both types of template molecules were present. The proportion of singlet beads that hybridized to at least one of the probes was 2.9%, 4.3%, and 20.3% in (FIG. 3B) to (FIG. 3D), respectively. The FSC and SSC plots in (FIG. 3A) represent the same beads analyzed in (FIG. 3D).

(FIG. 5A) Mixtures of PCR products containing 0% to 4% L alleles of MID42 were used for BEAMing. Flow cytometry such as that shown in FIG. 3 was used to determine the fraction of singlet beads that were red (y-axis). The proportion of singlet beads that hybridized to at least one of the probes varied from 3.2% to 4.3%. (FIG. 5B and FIG. 5C) Beads were sorted with the FACS Vantage SE instrument and individual red or green beads were used as templates for conventional PCR employing the forward and reverse primers listed in FIG. 8. Red beads generated only the S allele sequence (FIG. 5B; SEQ ID NO: 1) while green beads generated only the L allele sequence (FIG. 5C; SEQ ID NO: 2).

FIG. 6A shows the bubbles that have fluorescents in them. FIG. 6B shows a darkfield image of the bubbles with one of the bubbles containing a bead in it. After breaking the emulsions, the droplets containing magnetic beads can be recovered by centrifugation and size fractionated through filtration or flow sorting.

FIG. 8 shows oligonucleotides used.

DETAILED DESCRIPTION OF THE INVENTION

Figure 1:
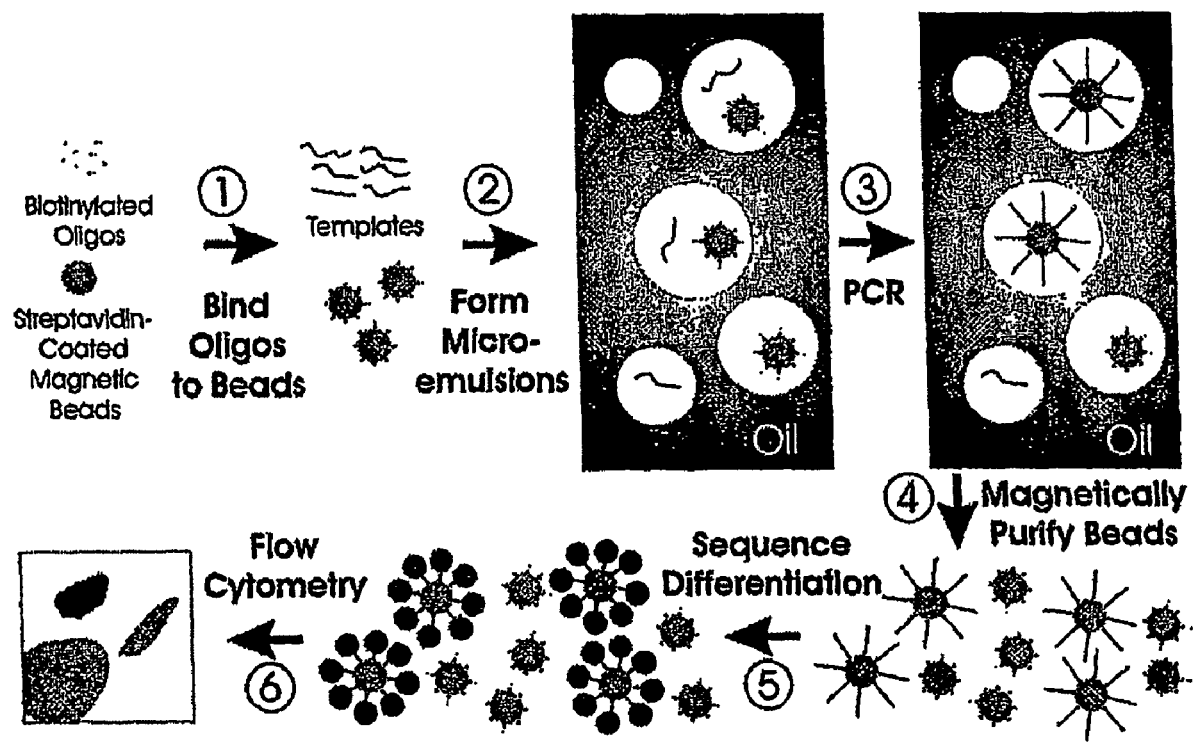
FIG. 1 is a schematic drawing of the BEAMing method. Step 1—Magnetic beads covalently coated with streptavidin are bound to biotinylated oligonucleotides ("oligos"). Step 2—An aqueous mix containing all the necessary components for PCR plus primer-bound beads and template DNA are stirred together with an oil/detergent mix to create microemulsions. The aqueous compartments (white circles in the gray oil layer) contain an average of <1 template molecule and <1 bead. Red and green templates represent two template molecules whose sequences differ by one or many nucleotides. Step 3—The microemulsions are temperature cycled as in a conventional PCR. If a DNA template and a bead are present together in a single aqueous compartment, the bead bound oligonucleotides act as primers for amplification. The straight red and green lines connected to the beads represent extension products from the two different kinds of templates. Step 4—The emulsions are broken and the beads are purified with a magnet. Step 5—After denaturation, the beads are incubated with oligonucleotides that can distinguish between the sequences of the different kinds of templates. Fluorescently-labeled antibodies are then used to label the bound hybridization probes. This renders the beads containing PCR product as red or green upon appropriate laser excitation. Step 6—Flow cytometry is used to count the red and green beads.

The inventors describe herein a digital technology, called BEAMing, that has the power to assess millions of molecules and can be generally applied to the study of genetic variation. The technology involves conversion of single DNA molecules to single beads each containing thousands of copies of the sequence of the original DNA molecule. The number of variant DNA molecules in the population can then be assessed, for example, by staining the beads with fluorescent probes and counting them using flow cytometry. Beads representing specific variants can be optionally recovered through flow sorting and used for subsequent confirmation and experimentation.

Beads according to the present invention are also known as microspheres or microparticles. Particle sizes can vary between about 0.1 and 10 microns in diameter. Typically beads are made of a polymeric material, such as polystyrene, although nonpolymeric materials such as silica can also be used. Other materials which can be used include styrene copolymers, methyl methacrylate, functionalized polystyrene, glass, silicon, and carboxylate. Optionally the particles are superparamagnetic, which facilitates their purification after being used in reactions.

Beads can be modified by covalent or non-covalent interactions with other materials, either to alter gross surface properties, such as hydrophobicity or hydrophilicity, or to attach molecules that impart binding specificity. Such molecules include without limitation, antibodies, ligands, members of a specific-binding protein pair, receptors, nucleic acids. Specific-binding protein pairs include avidin-biotin, streptavidin-biotin, and Factor VII-Tissue Factor.

Beads, after being prepared according to the present invention as product beads, have more than one copy of the same nucleic acid molecule bound to them. Preferably each bead is bound to at least 10, 50, 100, 500, or 1000 molecules of the same nucleic acid sequence. In some circumstances some of the product beads are bound to more than one type of nucleic acid molecule. These product beads are generally less useful in the analysis of ratios of genetic sequences in a population of genetic sequences. Such product beads can be readily discriminated and so will not distort the analysis.

A population of product beads will often comprise two or more types of nucleic acids. Such a population is heterogeneous with respect to the nucleic acids. Desirably, a substantial proportion of the product beads comprise only one type of nucleic acid per bead. A substantial proportion can be for example, at least 1%, at least 5%, at least 10%, or at least 50%. A product bead with only one type of nucleic acid per bead is termed homogeneous. Homogeneous beads with only one type of nucleic acid per bead include those with nucleic acids containing errors due to errors in polymerase chain reaction. A product bead with two types of nucleic acid per bead is termed heterogeneous. Although not wishing to be bound by any particular theory, heterogeneous product beads are thought to result from aqueous compartments which have more than two molecules of template of non-identical sequence. A population of product beads can be heterogeneous as a population but contain individual product beads that are homogeneous Individual product beads preferably comprise more than one copy of template analyte molecule. Each bead may comprise at least 10, at least 50, at least 100, at least 500, or at least 1000 copies of template analyte. If the bead is homogeneous, each of those copies will be identical.

Populations of product beads can be maintained in a liquid suspension. Alternatively they can be sedimented and dried or frozen. The latter alternatives may be beneficial for storage stability.

Analysis of populations of product beads can be useful for distinguishing between many kinds of genetic variants. Polynucleotides can be distinguished which differ by as little as a single nucleotide polymorphism (SNP), by the presence or absence of a mutation, by the presence or absence of an insertion or deletion, by the presence or absence of a non-single nucleotide polymorphism. Thus populations of product beads may be heterogeneous with regard to these genetic variations.

One very convenient way for distinguishing genetic variants, i.e., determining a sequence feature of the analyte, is by differentially labeling the variants with fluorescent dyes. Such labeling can be accomplished by hybridization of a fluorescently labeled oligonucleotide probe to one species of polynucleotide. Alternatively, a fluorescently labeled antibody can be used to specifically attach to one oligonucleotide probe that hybridizes to a particular genetic variant. Such antibody binding can be, for example, mediated by a protein or polypeptide which is attached to an oligonucleotide hybridization probe. Of course, other means of labeling polynucleotides as are known in the art can be used without limitation. Another means of labeling different polynucleotide species is by primer extension. Primers can be extended using labeled deoxyribonucleotides, such as fluorescently labeled deoxyribonucleotides.

Populations of product beads can be used as templates. Template analyte molecules on the product beads can be analyzed to assess DNA sequence variations by hybridization, primer-extension methods, mass spectroscopy, and other methods commonly used in the art. Template analyte molecules on product beads can be employed for solid phase sequencing. In one solid phase sequencing technique, product beads are arrayed by placing them on slides spotted with complementary oligonucleotides. In another solid phase sequencing technique, product beads are placed into individual wells. In still another solid phase sequencing technique product beads are incorporated into acrylamide matrices (with or without subsequent polony formation). Sequencing reactions can be performed with any solid phase sequencing method, such as those using unlabeled nucleotide precursors (e.g., pyrosequencing, as described in Ronaghi et al., *Anal. Biochem.* 267: 65-71, 1999) or labeled nucleotides (e.g., photocleavable reagents described by Mitra et al., *Anal. Biochem.* 320:55-65, 2003). Product beads can thus be used for and facilitate multiple parallel sequencing. Product beads can also be used in sequencing employing Type IIS restriction endonucleases. Product beads can also be used to provide templates for conventional dideoxynucleotide sequencing. To obtain useful data upon sequence analysis, a homogeneous template population is desirable. To provide a homogenous template population, product beads can be diluted, separated, or otherwise isolated so that each sequencing reaction contains a single product bead. Alternatively, product beads can be sorted to provide populations of beads with a single species of template.

Oligonucleotide primers can be bound to beads by any means known in the art. They can be bound covalently or non-covalently. They can be bound via an intermediary, such as via a protein-protein interaction, such as an antibody-antigen interaction or a biotin-avidin interaction. Other specific binding pairs as are known in the art can be used as well. To achieve optimum amplification, primers bound to the bead may be longer than necessary in a homogeneous, liquid phase reaction. Oligonucleotide primers may be at least 12, at least 15, at least 18, at least 25, at least 35, or at least 45 nucleotides in length. The length of the oligonucleotide primers which are bound to the beads need not be identical to that of the primers that are in the liquid phase. Primers can be used in any type of amplification reaction known in the art, including without limitation, polymerase chain reaction, isothermal amplification, rolling circle amplification, self-sustaining sequence replication (3SR), nucleic acid sequence-based amplification (NASBA), transcription-mediated amplification (TMA), strand-displacement amplification (SDA), and ligase chain reaction (LCR).

Microemulsions are made by stirring or agitation of oil, aqueous phase, and detergent. The microemulsions form small aqueous compartments which have an average diameter of 0.5 to 50 microns. The compartments may be from 1 to 10 microns, inclusive, from 11 to 100 microns, inclusive, or about 5 microns, on average. All such compartments need not comprise a bead. Desirably, at least one in 10,000 of said aqueous compartments comprise a bead. Typically from 1/100 to 1/1 or from 1/50 to 1/1 of said aqueous compartments comprise a bead. In order to maximize the proportion of beads which are homogeneous with respect to oligonucleotide, it is desirable that on average, each aqueous compartment contains less than 1 template molecule. Aqueous compartments will also desirably contain whatever reagents and enzymes are necessary to carry out amplification. For example, for polymerase chain reaction (PCR) the compartments will desirably contain a DNA polymerase and deoxyribonucleotides. For rolling circle amplification a DNA polymerase and a generic DNA circle may be present.

Emulsions can be "broken" or disrupted by any means known in the art. One particularly simple way to break the emulsions is to add more detergent. Detergents which can be used include, but are not limited to Triton X100, Laureth 4, Nonidet.

Sample DNA for amplification and analysis according to the present invention can be genomic DNA, cDNA, PCR products of genomic DNA, or PCR products of cDNA, for example. Samples can be derived from a single individual, for example, from a body sample such as urine, blood, sputum, stool, tissue or saliva. Samples can also be derived from a population of individuals. The individuals can be humans, but can be any organism, plant or animal, eukaryotic or prokaryotic, viral or non-viral.

Any type of probe can be used for specific hybridization to the amplified polynucleotides which are bound to the beads. Fluorescently labeled probes are useful because their analysis can be automated and can achieve high throughput. Fluorescence activated cell sorting (FACS) permits both the analysis and the isolation of different populations of beads. One type of fluorescently labeled probe that can be used is a modified molecular beacon probe. These probes have stem-loop structures and an attached fluorescent moiety on the probe, typically on one end of the probe, sometimes attached through a linker. Unlike standard molecular beacon probes, modified molecular beacon probes do not have a quenching moiety. The modified molecular beacon probe can have the fluorescent moiety attached on either end of the probe, 5' or 3'. One such probe will hybridize better to a wild-type sequence than to a mutant. Another such probe will hybridize better to a mutant sequence than to the wild type. Still other probes will preferably hybridize to one polymorphic variant over another.

Figure 5:
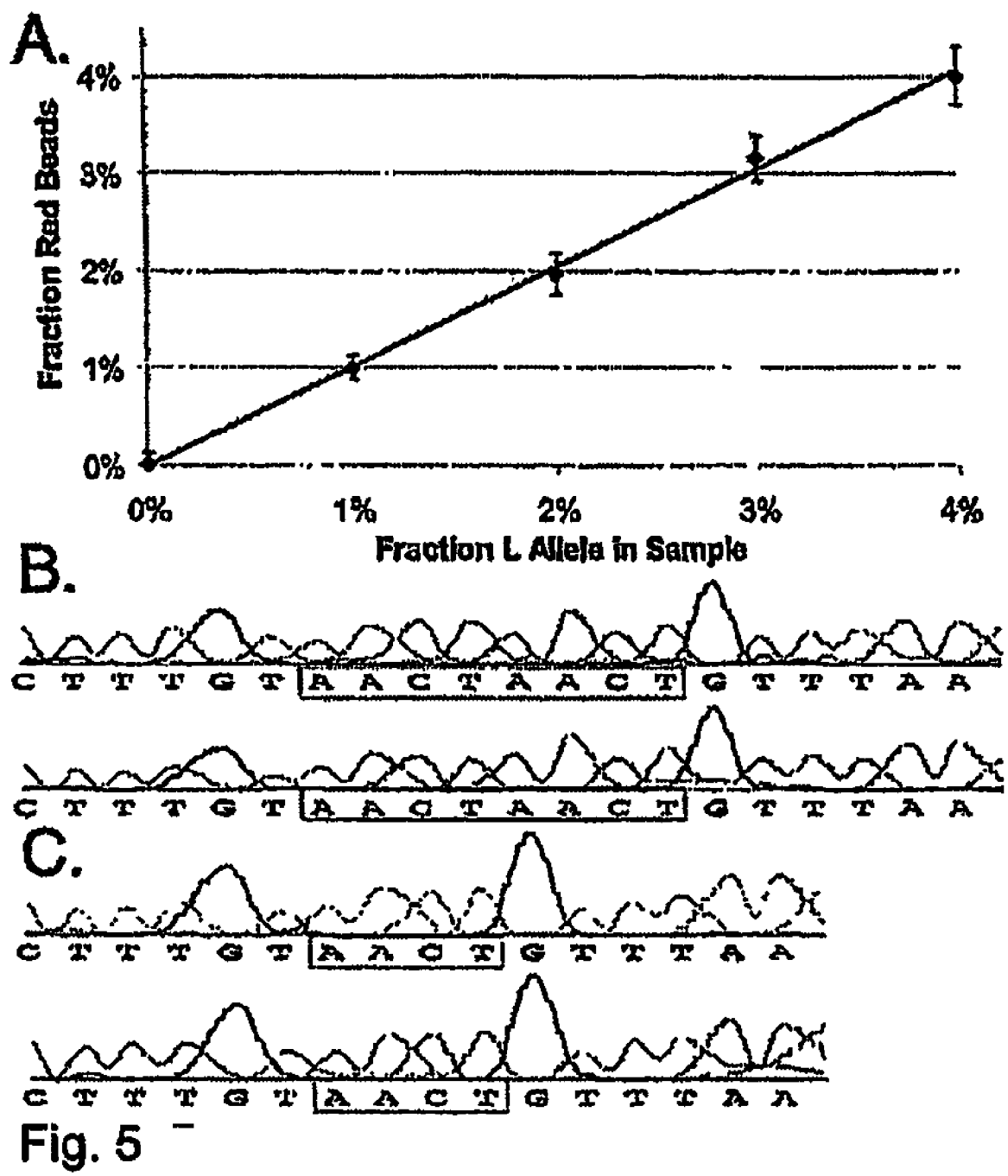
FIG. 5A to FIG. 5C show detection and validation of variants present in a minor fraction of the DNA population.
Figure 6:
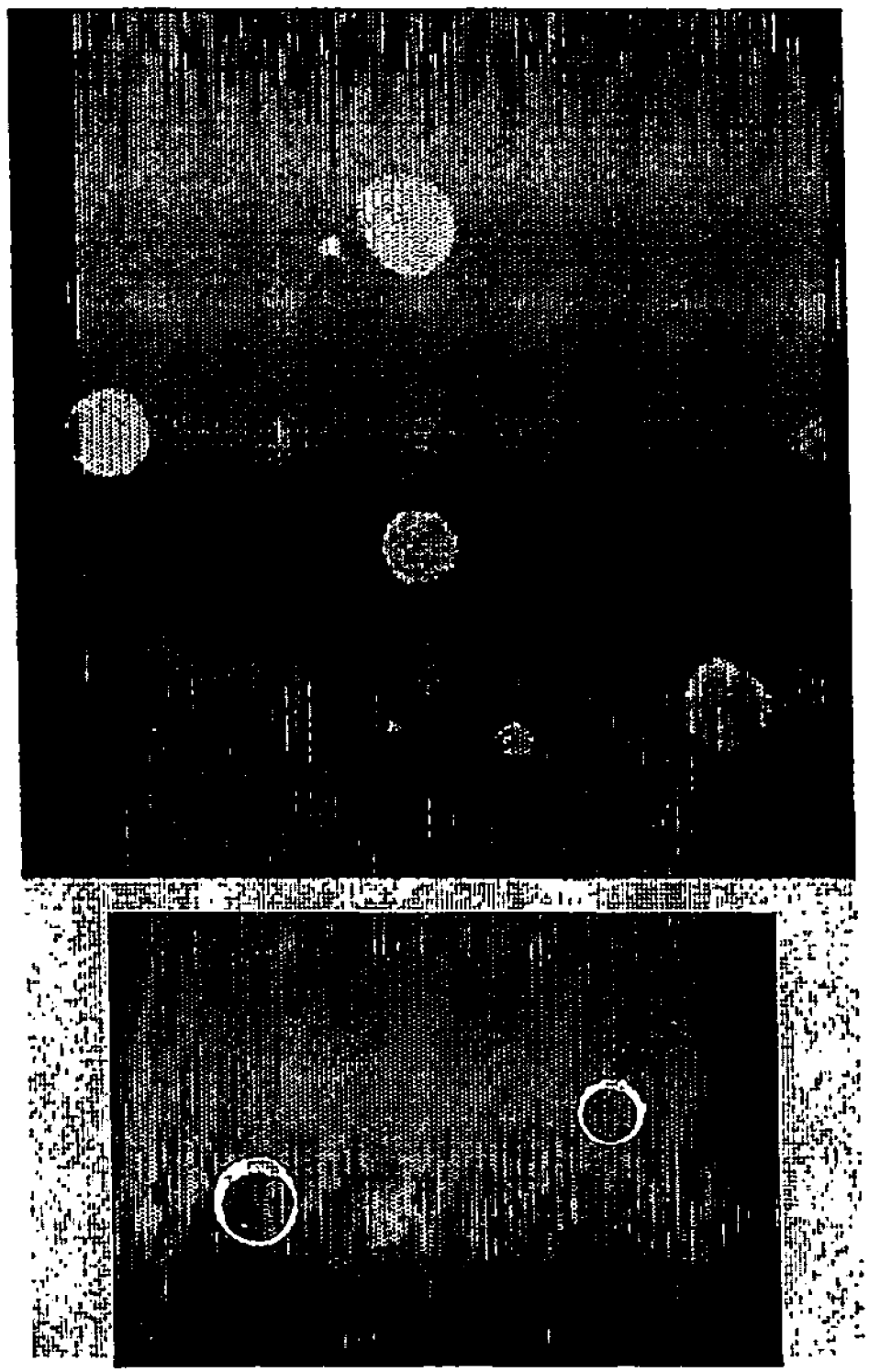
FIG. 6A to 6B demonstrate the use of agar in the aqueous phase of the microemulsions. Emulsion bubbles that were formed by including 1.5% agarose in the aqueous compartment are shown.

The method of the present invention provides a reliable and sensitive assay for measuring variations in genes and transcripts. It requires no instrumentation other than machines that are widely available. There are several other advantages of this approach. First, the sensitivity can be increased to meet the particular specifications of an assay simply by analyzing more beads. Such sensitivity is limited only by the error rate of the polymerases used for amplification. Second, the data obtained can be used not only to demonstrate that a variant is present in a particular population of DNA molecules, but also quantifies the fraction of variant DNA molecules in that population (FIG. 5A). Such quantification is not possible with techniques that destroy or ignore the wild type molecules as part of the assay, such as those that use allele specific priming or endonuclease digestion during PCR. Third, the beads containing variant alleles can easily be purified through flow sorting. Such recovery is difficult with digital techniques that count molecules deposited on microscope slides. And finally, the method is automatable.

Figure 2:
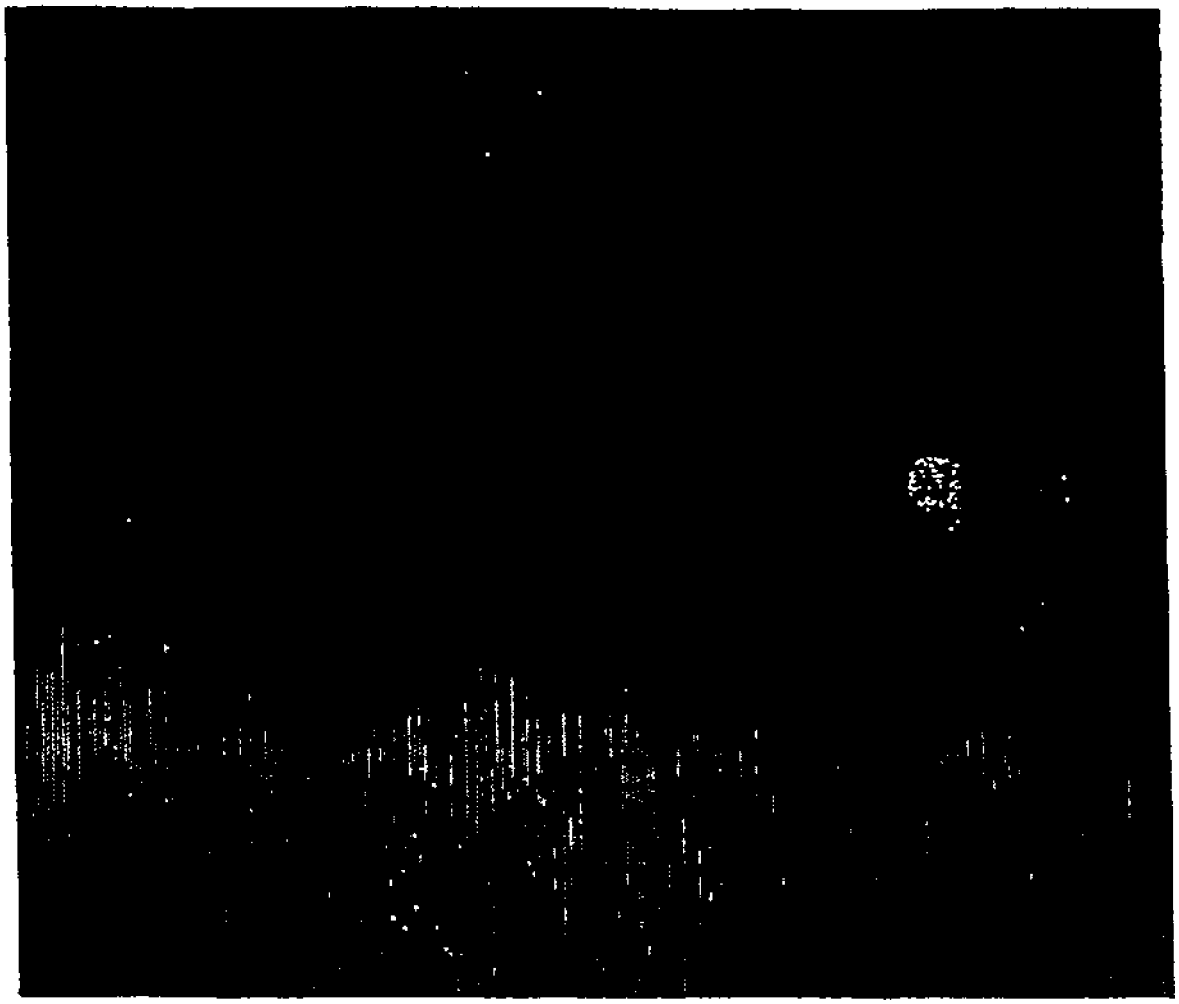
FIG. 2 is a photograph of a typical microemulsion. Microemulsions were made as described infra with the exception that the aqueous compartments contained cascade blue-labeled dCTP and the beads were pre-labeled with R-phycoerythrin (red) or Alexa 488 (green). One microliter of microemulsion was deposited in 1 microliter of oil on a microscope slide prior to photography. Of the seven aqueous compartments visible in this picture, two contain beads. Note the heterogeneous size of the aqueous compartments (beads are 1.05 microns in diameter).

Several modifications of the basic principles described here can be envisioned that will further simplify the technology or widen its applications. For example, microemulsions were made by stirring water/oil/detergent mixes. The sizes of the resultant aqueous compartments were somewhat heterogeneous, as illustrated in FIG. 2. A relatively large number of beads containing PCR products of both alleles are obtained from large compartments because they are more likely to contain >1 template molecule than smaller compartments. Though this is not a problem for the analysis of uncommon variants, it does pose a problem when the variant to be analyzed is present in a substantial fraction of the DNA molecules. For example, it is easy to distinguish a population containing 2% of allele A and 98% of allele B from one that contains 0% of allele A (FIG. 5A). But it is more difficult to distinguish a population that contains 48% of allele A and 52% of allele B from a population that contains 50% of allele A; the large number of heterozygote beads formed in the latter analysis diffuse the boundaries of the pure red and green channels. This limit to accuracy can be overcome through the preparation of more uniformly sized aqueous compartments. Sonication or pressure-driven emulsifiers can make more uniform compartments.

Though flow cytometry requires only seconds to minutes per sample, multiple parallel analyses could facilitate throughput. Novel particle counting designs may prove useful for this purpose. Another way to increase throughput would be to physically separate the beads that contained PCR products prior to flow cytometry. This could be accomplished with proteins such as antibodies or streptavidin that bind to modified nucleotides incorporated into the PCR product during amplification.

The methods of the invention can be applied to genes or transcripts of any organism or population of organisms. These include without limitation: humans, rodents, ungulates, mammals, primates, cows, goats, pigs, rats, mice, yeast, poultry, fish, shellfish, digs, cats, zebrafish, worms, algae. It can also be used to quantify epigenetic alterations, such as methylation, if DNA is first treated with bisulfite to convert methylated cytosine residues to thymidine. Beads generated from random fragments of whole genomes (24), rather than from individual genes as described above, could be used to identify gene segments that bind to specific DNA-binding proteins (25). And if the product beads are used in compartmentalized in vitro transcription-translation reactions, variant proteins can be bound to beads containing the corresponding variant DNA sequences (23). This could allow facile flow cytometric evaluation of rare mutations using antibodies that distinguished between wild type and mutant gene products (26).

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

EXAMPLES

Example 1

Materials and Methods

Step 1—Coupling oligonucleotides to beads. Superparamagnetic beads of 1.05+/−0.1 um in diameter, covalently bound to streptavidin, were purchased from Dynal Biotech, Inc. (650.01, Lake Success, N.Y.). Beads were washed once with 1×PCR buffer (53286, Invitrogen, Carlsbad, Calif.) then suspended in Bind and Wash Buffer (BWB) (5 mM Tris-HCl, 0.5 mM EDTA, 1.0 M NaCl, pH 7.5). Beads were incubated in BWB for 30 min at room temperature in the presence of 10 uM oligonucleotides (FIG. 8). These oligonucleotides were modified with a dual biotin group at the 5' end with the biotin groups separated by a six-carbon linker (IDT, Coralville, Iowa). After binding, the beads were washed 3 times with 1×PCR buffer to thoroughly remove unbound oligonucleotides.

Step 2—Preparing microemulsions. Microemulsions for PCR were prepared by slight modifications of previously described methods (14) (15). The oil phase was composed of 4.5% Span 80 (S6760, Sigma, St. Louis, Mo.), 0.40% Tween 80 (Sigma S-8074), and 0.05% Triton X-100 (Sigma T-9284) in mineral oil (Sigma M-3516). The oil phase was freshly prepared each day. The aqueous phase consisted of 67 mM Tris-HCl (pH 8.8), 16.6 mM NH4SO4, 6.7 mM MgCl2, 10 mM β-mercaptoethanol, 1 mM dATP, 1 mM dCTP, 1 mM dGTP, 1 mM dTTP, 0.05 uM forward primer, 25 uM reverse primer, 45 units Platinum Taq (Invitrogen 10966-034), various amounts of template DNA (see results), and ~$10^8$ oligonucleotide-coupled beads in a total volume of 300 ul. The forward primer was an oligonucleotide whose sequence was identical to the 3' 20-22 nt of that described in step 1 and was not modified with biotin.

Water-in-oil microemulsions were prepared by drop wise addition of 200 microliters of the aqueous phase to 400 microliters of the oil phase previously placed in a 2 ml round bottom cryogenic vial (430661, Corning, Corning, N.Y.). The drop wise addition was performed over ~one minute while the mixture was being stirred at 1400 RPM with a magnetic microstir bar (58948-353, VWR, Plainfield, N.J.) on a VWR model 565 Magnetic Stirrer. After the addition of the aqueous phase, the mixture continued to be stirred for a total time of 30 minutes. Two emulsions were made at once by placing two tubes in a rack placed at the center of the magnetic stirrer.

Step 3—PCR cycling. The emulsions were aliquoted into five wells of a 96 well PCR plate, each containing 100 ul. PCR was carried out under the following cycling conditions: 94° C. for 2 minutes; 40 cycles of 94° C. for 15 seconds, 57° C. for 30 seconds, 70° C. for 30 seconds. The PCR products analyzed in this study ranged from 189 to 239 bp.

Step 4—Magnetic capture of beads. After PCR cycling, the microemulsion from five wells of a PCR plate were pooled and broken by the addition 800 microliters of NX buffer (100 mM NaCl containing 1% Triton X-100, 10 mM Tris-HCl, pH 7.5, 1 mM EDTA) in a 1.5 ml tube (Corning 430909). After vortexing for ~20 sec. the beads were pelleted by centrifugation in a microcentrifuge at 8000 rpm (5000 g) for 90 seconds. The top oil phase and all but ~300 microliters of the aqueous phase was removed from the tube and 600 microliters of NX buffer was added. After vortexing for 20 sec. and centrifugation for 90 sec., the top oil phase and all but ~300 microliters of the aqueous phase was removed. The addition of 600 microliters NX buffer, vortexing, and centrifugation was repeated once more and the top oil portion and all but ~300 microliters of the aqueous phase was removed. The tube was then placed on a magnet (Dynal MPC-S) and the rest of the supernatant was carefully pipetted off. The beads were washed an additional 3 times with 1×PCR buffer using magnetic separation rather than centrifugation and finally resuspended in 100 microliters of 1×PCR buffer.

Step 5—Sequence differentiation. Two oligonucleotide probes were used for each reaction. One was 5'-labeled with 6-carboxyfluorescein (6-FAM) and was specific for one allele while the second was 5'-labeled with biotin and was specific for the other allele. Probes were synthesized by IDT. The 30 microliters hybridization reactions contained 10 uM of each probe and 5-25 million beads in 1×PCR buffer. Reactions were performed in PCR plates on a thermal cycler by heating to 94° C. for 30 seconds then cooling to 75° C. at a rate of 0.5° C. per second, cooling to 45° C. at 0.2° C. per second, and finally cooled to 30° C. at 1° C. per second. All subsequent steps were performed at room temperature. The reactions were transferred to a 96 well Costar plate (Corning 3797) and placed on a 96 well magnet. Beads were collected magnetically by exposing them to the magnet for 2 minutes. The supernatant was removed and the beads washed 3 times with 1×PCR buffer by pipetting them and collecting for two minutes. They were finally resuspended in 100 microliters B-PCR buffer (1 mg/mL BSA in 1×PCR buffer). The beads were then incubated for 10 minutes in a total volume of 100 microliters B-PCR buffer containing 3 ug of Alexa-488 rabbit anti-fluorescein antibody (Molecular Probes A-11090, Eugene, Oreg.) and 3 ug of Nutravidin labeled with R-phycoerythrin (Molecular Probes A-2660) in B-PCR buffer. The beads were washed three times and resuspended in B-PCR buffer as described above. They were then incubated for ten minutes in a total volume of 100 microliters B-PCR buffer containing 6 ug of Alexa 488-conjugated chicken anti-rabbit antibody (Molecular Probes A-21441) and 3 ug of biotinylated goat anti-avidin antibody (BA-0300, Vector Laboratories, Burlingame, Calif.). The beads were washed three times and resuspended in B-PCR buffer as described above. They were then incubated for ten minutes in a total volume of 100 microliters B-PCR buffer containing 3 ug of an Alexa 488-conjugated goat anti-chicken antibody (Molecular Probes A-11039) and 3 micrograms of R-phycoerythrin-labeled streptavidin (Molecular Probes S-866). This solution was then washed an additional 3 times with 1×PCR buffer and resuspended in 20 microliters of 1×PCR buffer.

Step 6—Flow Cytometry. The bead suspension was diluted to a concentration of ~106-107 beads per ml in 10 mM Tris-HCl, 1 mM EDTA (351-010-131, Quality Biological, Inc., Gaithersburg, Md.) and analyzed using a LSR instrument (BD Biosciences, Franklin Lakes, N.J.). The instrument was set up for standard two-color analysis using an argon laser and optical filters that distinguished between the two fluorescent dyes. No spectral deconvolution was required as the major bead populations were well-separated. In some cases, scanning was performed with FACScan or FACSCalibur instruments (BD Biosciences), yielding equivalent results. Sorting was carried out with a FACS Vantage SE instrument (BD Biosciences).

Template preparation and sequence analyses. Human genomic DNA was purified with DNeasy (69504, Qiagen, Valencia, Calif.). RNA was purified with Quickprep (27-9255-01, Amersham Biosciences, Piscataway, N.J.). Reverse transcription of RNA was performed using Superscript II reverse transcriptase (Invitrogen 18064014) according to the manufacturer's instructions. PCR using genomic DNA or reverse transcripts as templates was performed as described (7). PCR products to be used as templates for BEAMing or for sequencing were purified with QIAquick (Qiagen 28104). Sequencing reactions were performed using Big Dye v3.0 reagents (Applied Biosystems, Foster City, Calif.) and analyzed by capillary electrophoresis (Spectrumedix 9600, State College, Pa.).

Example 2

Results

Step 1—Coupling oligonucleotides to beads. We used streptavidin-beads because of the simplicity of coupling biotinylated oligonucleotides to them. Oligonucleotides with just a single 5' biotin group were found to dissociate from the beads during temperature cycling, while oligonucleotides labeled with dual biotin groups at their 5' end (separated by a six-carbon linker) were stable to cycling. As determined by fluoroscopic measurements of oligonucleotides doubly labeled with 6-FAM and biotin, ~105 oligonucleotide molecules were bound to each bead. We found that short oligonucleotides (20 bases) did not work as well for priming as longer ones (41 bp), perhaps because of steric hindrance at the bead surface. It is likely that amino-, sulfhydryl-, or carboxyl-modified oligonucleotides covalently coupled to beads modified with corresponding reactive groups could also function as bead-bound primers for BEAMing.

Step 2—Preparing microemulsions. The size of the individual aqueous compartments ranged from less than 1 micron to >10 microns in diameter (FIG. 2). We estimated that an emulsion comprising 200 microliters of aqueous solution and 400 microliters of oil would contain ~$3\times10^9$ compartments with an average diameter of 5 microns. Approximately $10^8$ beads were included in each emulsion, so that only one in ~30 compartments contained a bead. The optimal amount of template was experimentally determined to be ~$5\times10^8$ molecules, so that one in ~six compartments contained a template molecule.

Step 3—PCR cycling. PCR priming by oligonucleotides coupled to beads was found to be very inefficient compared to the priming by the same oligonucleotides when free in solution. For this reason, a small amount of non-biotinylated forward primer identical in sequence to the biotinylated oligonucleotide coupled to the beads was included in the reactions. This facilitated the first few rounds of amplification of the single template within each aqueous compartment. In the absence of additional primer, no detectable amplification on the beads was generated. Conversely, if too much additional primer was included, no amplification on the beads occurred because of competition with the primers in solution. An excess of the reverse primer was included in the aqueous compartment to maximize the probability that bead-bound oligonucleotides extended by polymerase would serve as templates for further amplification cycles.

Step 4—Magnetic capture of beads. There are several ways to break water-in-oil emulsions, including extraction with organics (14). We found that simply adding non-ionic detergents produced phase separations without any detectable modification of the beads or DNA molecules bound to them. By measuring the amount of DNA that could be released from the beads following restriction endonuclease digestion, we estimate that >10,000 extended PCR products were present, on average, per bead.

Step 5—Sequence differentiation. Most fluorescence-based methods for distinguishing alleles in homogeneous or two-phase assays can be used to assess allelic variation captured on beads. These methods include single nucleotide extension, allele specific priming, or hybridization. We generally employed hybridization of fluorescein-conjugated or biotin-conjugated oligonucleotides for discrimination. As shown in FIG. 1 and FIG. 8, these oligonucleotides had a stem-loop structure, with the middle of the loop containing the variant nucleotide(s). This design was based on studies of Molecular Beacons wherein a stem-loop structure was shown to markedly improve allelic discrimination (16). The oligonucleotides we used differed from Molecular Beacons in that there was no need for a quenching group. Such quenching is required for homogeneous assays when unhybridized oligonucleotides cannot be removed from the reactions prior to assay but is not necessary for solid phase assays such as those employed with beads.

Step 6—Flow Cytometry. Optimum results in flow cytometry depend on high fluorescent signals on the beads. We generally enhanced the fluorescence emanating from the hybridization probes with secondary reagents. For example, Alexa 488-labeled antibodies were used to enhance the signals emanating from fluorescein-coupled oligonucleotide probes. Similarly, R-phycoerythrin-labeled streptavidin was used to generate a signal from biotin-labeled oligonucleotide probes. Flow cytometers equipped with two or three lasers and appropriate filters have the capacity to distinguish multiallelic loci and to perform multiplex analysis of several genes simultaneously. The newest generation of flow cytometers can also analyze >70,000 events per second. In addition to the analytical power of flow cytometry, FACS instruments can separate specific populations of beads for further analysis.

Example 3

Characteristics of Microemulsions

Pilot experiments demonstrated that simply stirring the water-oil mixtures described in Materials and Methods produced very stable microemulsions of a size compatible with that of the beads. In the experiment shown in FIG. 2, the aqueous compartment contained a blue dye and 1 micron magnetic beads that were labeled by binding to an oligonucleotide that was biotinylated at its 5' end and labeled with fluorescein at its' 3' end The appearance of emulsions immediately after their formation is shown in FIG. 2. As expected, this appearance was unchanged after temperature cycling during PCR (15). Most aqueous compartments contained no beads, as expected from the figures provided in the previous section. Those compartments that did contain beads generally contained only one, though a fraction contained more, as expected from a Poisson distribution and non-uniform aqueous compartment sizes. "Heterozygous" beads containing PCR products representing both alleles are produced when two or more DNA template molecules are contained within a single aqueous compartment. Such heterozygotes can compromise the accuracy of the analyses under some circumstances (see Discussion).

Example 4

Detection of Homozygotes and Heterozygotes

Figure 3:
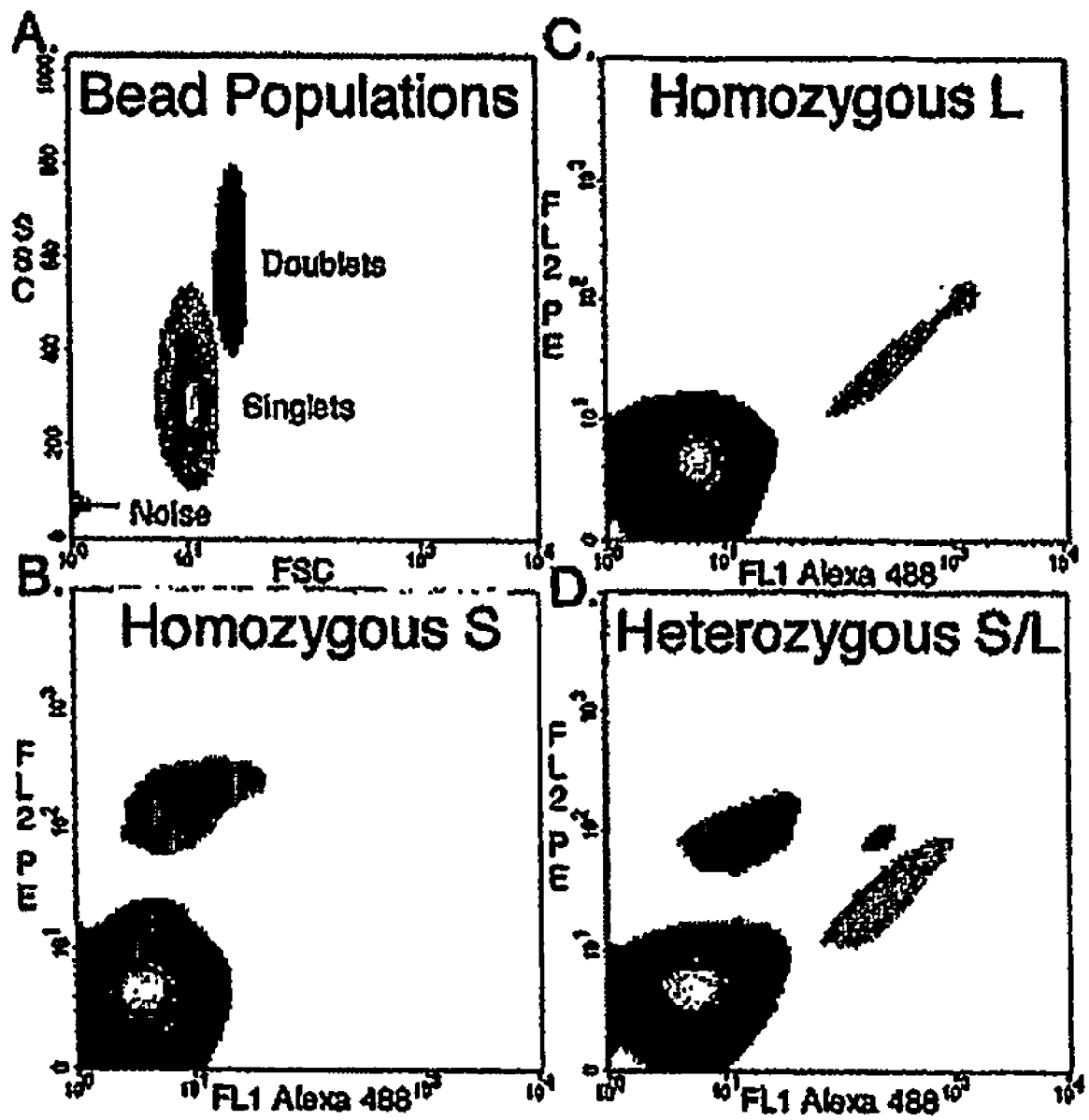
FIG. 3A to FIG. 3D show density plots of flow cytometric data obtained from BEAMing. The locus queried in this experiment was MID42 and PCR products generated from genomic DNA were used as templates in the microemulsions.

FIG. 3 shows typical results obtained with human DNA samples. The MID42 marker used in this experiment was chosen from a collection of diallelic short insertion/deletion polymorphisms assembled by Weber and colleagues (17). These alleles are particularly simple to distinguish with hybridization probes because the two alleles at each locus differ by ~4 bases. The probe for the longer (L) allele was labeled with fluorescein (green) and the probe for the shorter (S) allele labeled with R-phycoerythrin (red).

FIG. 3A shows a plot of the side scatter vs. forward scatter of beads following BEAMing. In general, >75% of beads were dispersed as single particles, with the remainder aggregated in groups of two or more. Subsequent flow cytometric analysis was confined to the singlet beads, gated as outlined in FIG. 3A.

FIGS. 3B-D show density plots of gated beads generated with various templates. In FIG. 3B, a template from an individual homozygous for the L allele was included in the emulsion. Two populations of beads were apparent. 98% of the beads contained no PCR product (black) and the remaining 2% fluoresced in the FL1 channel (colored green in FIG. 3).

FIG. 3C represents the analysis of an individual homozygous for the S allele. Two populations of beads were again apparent, but this time the labeled population fluoresced in the FL2 channel (colored red in FIG. 3). FIG. 3D presents density plots from the analysis of an individual heterozygous at the MID42 locus. Four populations of beads are evident: the black region represents beads without any PCR product, the red region represents beads containing PCR products from the L allele, the green region represents beads containing PCR products from the S allele, and the blue region represents beads containing PCR products from both alleles. Beads containing PCR products from both alleles were derived from aqueous compartments which contained more than one template molecule. The number of blue beads increased in a non-linear fashion as more template molecules were added. At the extreme, when all aqueous compartments are saturated, virtually all beads will register as blue. Operationally, we found that the bead populations were most distinct when the number of beads containing any PCR product was <10% of the total beads analyzed.

Example 5

PCR Products, Genomic DNA or cDNA as Templates

The results shown in FIG. 3 were generated using PCR products made from human genomic DNA samples. As the ratio of the beads representing L alleles to those representing S alleles was 1.0 in this experiment, it was clear that the initial PCR did not preferentially amplify either allele. The use of PCR products rather than genomic DNA permitted large numbers of alleles to be amplified from even small quantities of starting DNA. In general, 10 to 100 picograms of PCR products of size 200 bp were found to be optimal for BEAMing, producing PCR-mediated extension of primers on ~1 to 10% labeled beads.

Figure 4:
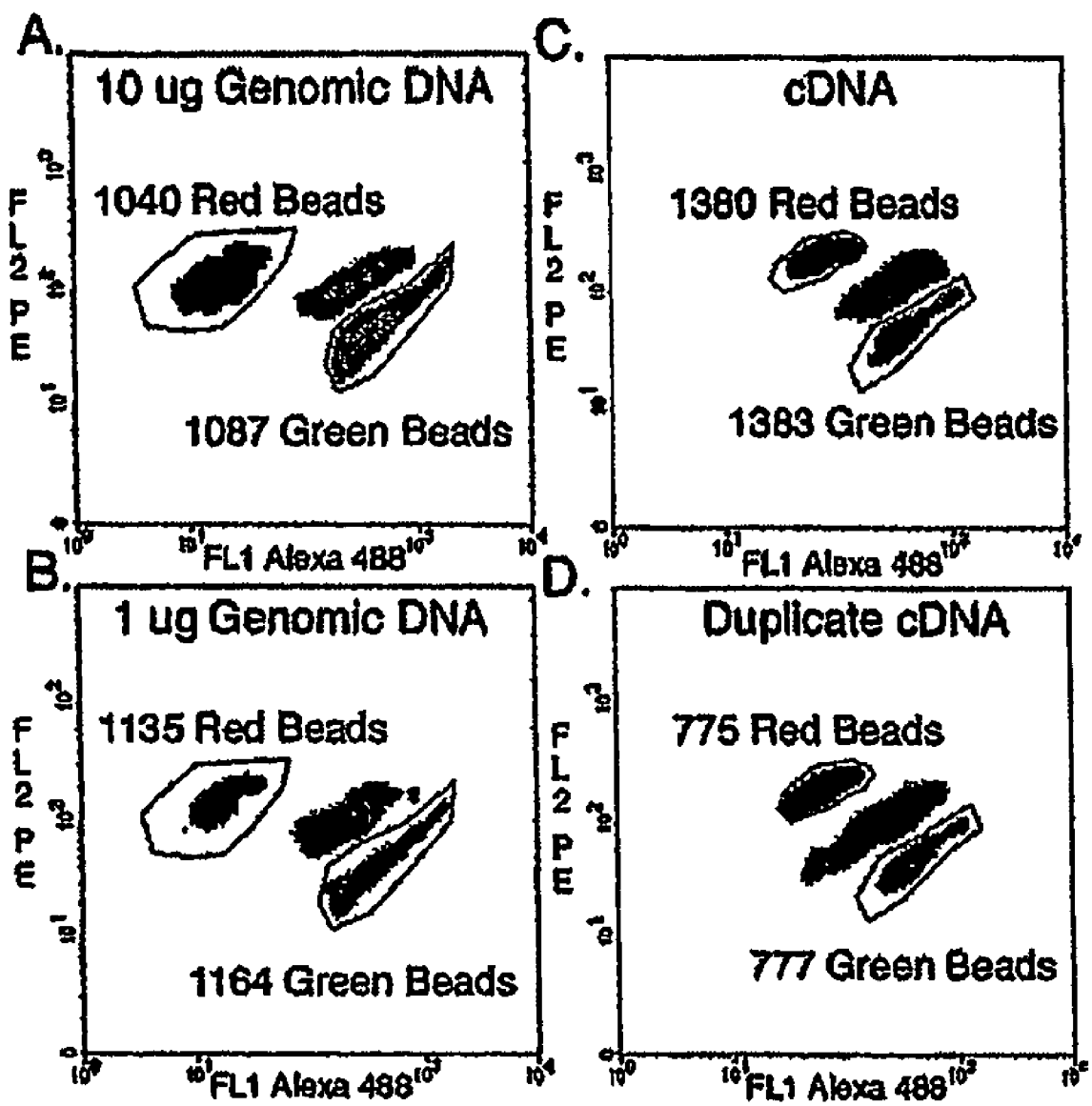
FIG. 4A to FIG. 4D show density plots of BEAMing using genomic DNA or RT-PCR products as templates. The data in (FIG. 4A) and (FIG. 4B) were generated by including 10 and 1 ug of human genomic DNA, respectively, in the microemulsions, querying the MID42 locus. The data in (FIG. 4C) and (FIG. 4D) were generated using emulsions that contained ~50 picograms of PCR products synthesized from cDNA of lymphoblastoid cells, querying the calpain-10 locus. The green and red regions correspond to the L and S alleles for MID42 and to the A and G alleles for calpain-10. The number of beads in the outlined regions containing red or green beads is shown in each case. The proportion of singlet beads that hybridized to at least one of the probes was 1.2%, 0.6%, 6.8% and 4.2% in (FIG. 4A) to (FIG. 4D), respectively. The outlined regions used for counting in (FIG. 4A) and (FIG. 4B) were identical, as were those used for (FIG. 4C) and (FIG. 4D). Beads that did not hybridize to any probe were gated out and therefore not evident in the graphs, while the region containing beads that hybridized to both probes is labeled blue.

In some situations it might be useful to use genomic DNA rather than PCR products as templates for BEAMing. The data in FIGS. 4A and B show flow cytometric data from an experiment wherein 10 ug or 1 ug of human genomic DNA was used as template for BEAMing at the MID42 locus. Patterns very similar to those shown in FIG. 3 were observed, though fewer beads were labeled than when PCR products were used as templates.

BEAMing could also be used to analyze variations in expression from the two alleles of a heterozygous individual. Heritable variations in the expression from individual alleles of the same gene have been shown to occur often in humans (18) and mice (19) and can have significant phenotypic effects (20). The results shown in FIGS. 4C and D show that PCR products made from reverse-transcribed mRNA can be used for BEAMing. In this case, calpain-10 transcripts differing by a single nucleotide polymorphism (SNP) were analyzed. For SNPs like these, probes that incorporated an extra mismatched nucleotide adjacent to the polymorphic nucleotide (see FIG. 8) can enhance the distinction between alleles (21) (22). The results from two independent emulsions made with aliquots of the same RT-PCR product are shown to illustrate reproducibility. Though the number of beads that functioned as templates in BEAMing varied up to 3-fold among experiments with identical templates, the proportion of beads representing the two alleles was reproducible (775 A allele beads to 690 G allele beads in FIG. 4C and 1380 A allele beads to 1227 G allele beads in FIG. 4D) respectively).

Example 6

Analysis of Minor Variants in a DNA Population

The analysis of uncommon variations is ideally suited for analysis via BEAMing because of the large number of molecules that can be independently analyzed while retaining a high signal-to-noise ratio. FIG. 5A shows representative data from templates representing 1%, 2%, 3%, and 4% of the L allele of MID42. The linearity of these measurements, with a correlation coefficient of 0.99, demonstrates the utility of this approach for such applications. We also applied this analysis to the detection of KRAS and could easily observe 0.1% mutants when spiked into a population of wt molecules (data not shown).

The rare beads representing the mutant alleles could not only be quantified but could also be purified for subsequent analysis. As a demonstration, samples of the beads enumerated in FIG. 5A were additionally assessed using a flow cytometer equipped with sorting capabilities. Beads were sorted and individual beads used as templates for conventional PCR using the same primers employed for BEAMing. As each bead contains thousands of bound template molecules, single beads were expected to generate robust PCR products (23) and this was experimentally confirmed. These PCR products were then subjected to sequencing. As shown in FIGS. 5B and C, green and red beads generated PCR products exclusively of the L and S types, respectively.

Example 7

Electrophoresis of Oligonucleotides Hyrbridized to Beads

Figure 7:
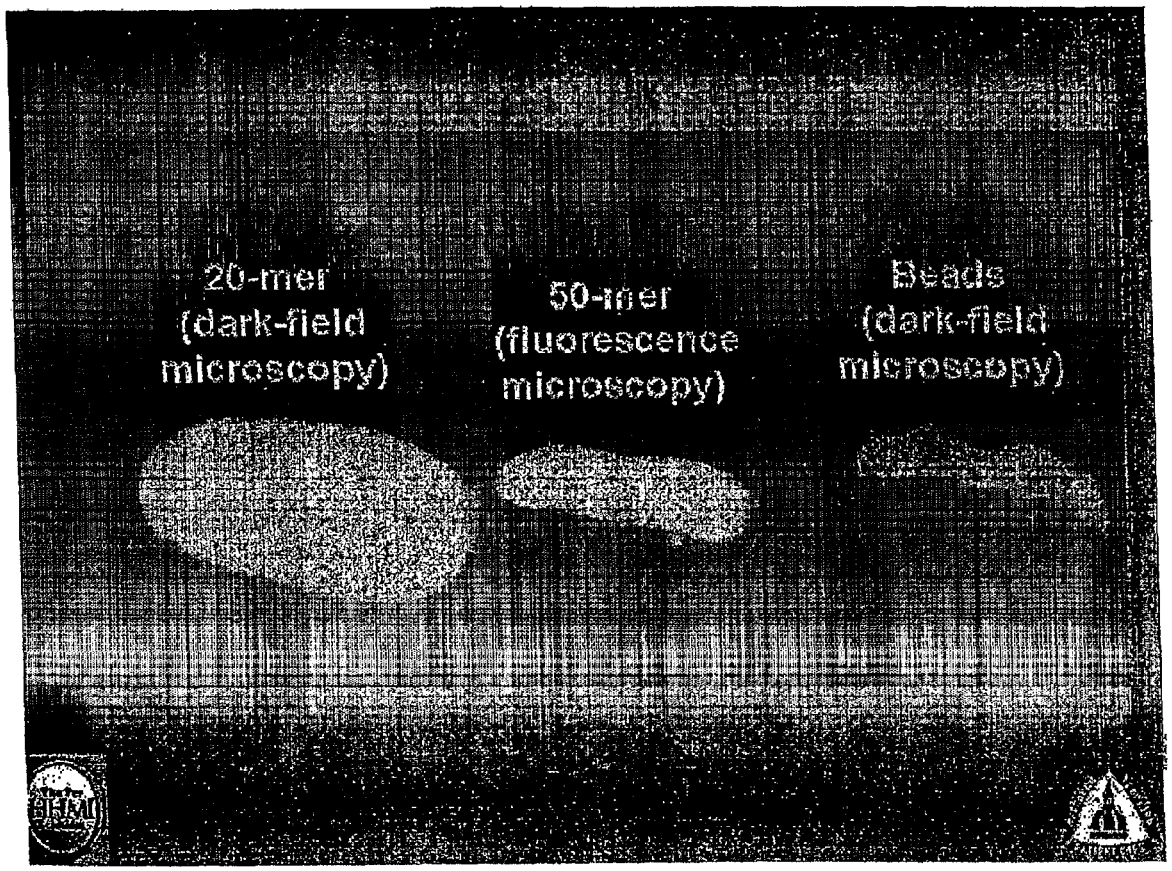
FIG. 7 shows denaturing electrophoresis of two FAM-labeled oligonucleotides, 50 and 20 bases in length, which had been hybridized to a 100 bp product on beads. The beads were embedded in an acrylamide gel in an oval shaped configuration and an electric field was applied The labeled oligonucleotides migrated off the beads and migrated a distance proportional to their size.

A 100 bp product was amplified on beads as described in Example 1, steps 1 through 4. Two FAM-labeled oligonucleotides (50 and 20 bases in length) were annealed to the 100 bp product on the beads. The beads were then embedded in an acrylamide gel (using conventional Tris-Borate-EDTA electrophoresis buffer) in an oval shaped configuration. An electric field (250 V) was applied under denaturing conditions for 3 minutes. The labeled oligonucleotides migrated off the beads and migrated a distance related to their sizes. See FIG. 7. There was little diffusion, as evidenced by the retention of the oval shape of the beads.

Example 8

Sequencing of Templates Immobilized to Beads

Sanger-type (dideoxynucleotide) sequencing is performed using as templates oligonucleotides which have been amplified on beads, as described in Example 1. Individual beads are subjected to primer extension conditions in the presence of dideoxynucleotide inhibitors. The beads are then subjected to electrophoresis under denaturing conditions to separate the dideoxynucleotide-terminated, primer extended oligonucleotides on the basis of length. A sequence is compiled based on the length of the primer extended oligonucleotides.

REFERENCES CITED

1. Collins, F. S., Patrinos, A., Jordan, E., Chakravarti, A., Gesteland, R. & Walters, L. (1998) *Science* 282, 682-689.
2. Vogelstein, B. & Kinzler, K. W. (2002) *The Genetic Basis of Human Cancer*(McGraw-Hill, Toronto).

3. Sidransky, D., Von Eschenbach, A., Tsai, Y. C., Jones, P., Summerhayes, I., Marshall, F., Paul, M., Green, P., Hamilton, S. R., Frost, P. & et al. (1991) *Science* 252, 706-709.
4. Ahlquist, D. A. & Shuber, A. P. (2002) *Clin Chim Acta* 315, 157-168.
5. Sidransky, D. (2002) *Nat Rev Cancer* 2, 210-219.
6. Chomyn, A. & Attardi, G. (2003) *Biochem Biophys Res Commun* 304, 519-529.
7. Vogelstein, B. & Kinzler, K. W. (1999) *Proc Natl Acad Sci USA* 96, 9236-9241.
8. Mitra, R. D., Butty, V. L., Shendure, J., Williams, B. R., Housman, D. E. & Church, G. M. (2003) *Proc Natl Acad Sci USA* 100, 5926-5931.
9. Li, H. H., Gyllensten, U. B., Cui, X. F., Saiki, R. K., Erlich, H. A. & Arnheim, N. (1988) *Nature* 335, 414-417.
10. Ruano, G., Kidd, K. K. & Stephens, J. C. (1990) *Proc Natl Acad Sci USA* 87, 6296-6300.
11. Jeffreys, A. J., Allen, M. J., Armour, J. A., Collick, A., Dubrova, Y., Fretwell, N., Guram, T., Jobling, M., May, C. A., Neil, D. L. & et al. (1995) *Electrophoresis* 16, 1577-1585.
12. Lizardi, P. M., Huang, X., Zhu, Z., Bray-Ward, P., Thomas, D. C. & Ward, D. C. (1998) *Nat Genet* 19, 225-232.
13. Jurinke, C., van den Boom, D., Cantor, C. R. & Koster, H. (2002) *Adv Biochem Eng Biotechnol* 77, 57-74.
14. Tawfik, D. S. & Griffiths, A. D. (1998) *Nat Biotechnol* 16, 652-656.
15. Ghadessy, F. J., Ong, J. L. & Holliger, P. (2001) *Proc Natl Acad Sci USA* 98, 4552-4557.
16. Tyagi, S., Bratu, D. P. & Kramer, F. R. (1998) *Nat Biotechnol* 16, 49-53.
17. Weber, J. L., David, D., Heil, J., Fan, Y., Zhao, C. & Marth, G. (2002) *Am J Hum Genet* 71, 854-862.
18. Yan, H., Yuan, W., Velculescu, V. E., Vogelstein, B. & Kinzler, K. W. (2002) *Science* 297, 1143.
19. Cowles, C. R., Joel, N. H., Altshuler, D. & Lander, E. S. (2002) *Nat Genet* 32, 432-437.
20. Yan, H., Dobbie, Z., Gruber, S. B., Markowitz, S., Romans, K., Giardiello, F. M., Kinzler, K. W. & Vogelstein, B. (2002) *Nat Genet* 30, 25-26.
21. Okimoto, R. & Dodgson, J. B. (1996) *Biotechniques* 21, 20-26.
22. Luo, J., Bergstrom, D. E. & Barany, F. (1996) *Nucleic Acids Res* 24, 3071-3078.
23. Sepp, A., Tawfik, D. S. & Griffiths, A. D. (2002) *FEBS Lett* 532, 455-458.
24. Kinzler, K. W. & Vogelstein, B. (1989) *Nucleic Acids Res* 17, 3645-3653.
25. Yang, X., Li, X., Prow, T. W., Reece, L. M., Bassett, S. E., Luxon, B. A., Herzog, N. K., Aronson, J., Shope, R. E., Leary, J. F. & Gorenstein, D. G. (2003) *Nucleic Acids Res* 31, e54.
26. Gite, S., Lim, M., Carlson, R., Olejnik, J., Zehnbauer, B. & Rothschild, K. (2003) *Nat Biotechnol* 21, 194-197.

---

We claim:

1. A method for analyzing nucleotide sequences, comprising:
   forming microemulsions comprising more than one species of analyte DNA molecules, such that a plurality of aqueous compartments comprise a single species of analyte DNA molecule;
   amplifying analyte DNA molecules in the microemulsions in the presence of reagent beads, wherein the reagent beads are bound to a plurality of molecules of a primer for amplifying the analyte DNA molecules, whereby product beads are formed which are bound to a plurality of copies of the single species of analyte DNA molecule;
   separating the product beads from analyte DNA molecules which are not bound to product beads;
   determining a sequence feature of the single species of analyte DNA molecule which is bound to the product beads by flow cytometry.

2. The method of claim 1 wherein the analyte DNA molecules are in a sample selected from the group consisting of urine, blood, sputum, stool, tissue, and saliva, of a eukaryotic organism.

3. A method for analyzing nucleotide sequences, comprising:
   forming microemulsions comprising more than one species of analyte DNA molecules, such that a plurality of aqueous compartments comprise a single species of analyte DNA molecule;
   amplifying analyte DNA molecules in the microemulsions in the presence of reagent beads, wherein the reagent beads are bound to a plurality of molecules of a primer for amplifying the analyte DNA molecules, whereby product beads are formed which are bound to a plurality of copies of the single species of analyte DNA molecule;
   separating the product beads from analyte DNA molecules which are not bound to product beads;
   determining a sequence feature of the single species of analyte DNA molecule which is bound to the product beads;
   isolating product beads which are bound to a plurality of copies of the single species of analyte DNA;
   amplifying the single species of analyte DNA molecule from the isolated product beads.

4. The method of claim 3 wherein the analyte DNA molecules are in a sample selected from the group consisting of urine, blood, sputum, stool, tissue, and saliva, of a eukaryotic organism.

5. A method for analyzing nucleotide sequences, comprising:
   forming microemulsions comprising more than one species of analyte DNA molecules, such that a plurality of aqueous compartments comprise a single species of analyte DNA molecule;
   amplifying analyte DNA molecules in the microemulsions in the presence of reagent beads, wherein the reagent beads are bound to a plurality of molecules of a primer for amplifying the analyte DNA molecules, whereby product beads are formed which are bound to a plurality of copies of the single species of analyte DNA molecule;
   separating the product beads from analyte DNA molecules which are not bound to product beads;
   determining a sequence feature of the single species of analyte DNA molecule which is bound to the product beads by hybridization to oligonucleotide probes which are differentially labeled.

6. The method of claim 5 wherein the analyte DNA molecules are in a sample selected from the group consisting of urine, blood, sputum, stool, tissue, and saliva, of a eukaryotic organism.

7. A method for analyzing nucleotide sequences, comprising:
   forming microemulsions comprising more than one species of analyte DNA molecules, such that a plurality of aqueous compartments comprise a single species of analyte DNA molecule;
   amplifying analyte DNA molecules in the microemulsions in the presence of reagent beads, wherein the reagent beads are bound to a plurality of molecules of a primer for amplifying the analyte DNA molecules, whereby product beads are formed which are bound to a plurality of copies of the single species of analyte DNA molecule;
   separating the product beads from analyte DNA molecules which are not bound to product beads;
   determining using flow cytometry an amount of product beads comprising the single species of analyte DNA molecule as a fraction of product beads.

8. The method of claim 7 wherein the analyte DNA molecules are in a sample selected from the group consisting of urine, blood, sputum, stool, tissue, and saliva, of a eukaryotic organism.

9. A method for isolating nucleotide sequences, comprising:
   forming microemulsions comprising more than one species of analyte DNA molecules, such that a plurality of aqueous compartments comprise a single species of analyte DNA molecule;
   amplifying analyte DNA molecules in the microemulsions in the presence of reagent beads, wherein the reagent beads are bound to a plurality of molecules of a primer for amplifying the analyte DNA molecules, whereby product beads are formed which are bound to a plurality of copies of the single species of analyte DNA molecule;
   separating the product beads from analyte DNA molecules which are not bound to product beads;
   isolating using fluorescence activated cell sorting product beads which are bound to a plurality of copies of the single species of analyte DNA molecule from product beads which are bound to a plurality of copies of a second species of analyte DNA molecule.

10. The method of claim 9 wherein the analyte DNA molecules are in a sample selected from the group consisting of urine, blood, sputum, stool, tissue, and saliva, of a eukaryotic organism.

11. A method for isolating nucleotide sequences, comprising:
forming microemulsions comprising more than one species of analyte DNA molecules, such that a plurality of aqueous compartments comprise a single species of analyte DNA molecule;
amplifying analyte DNA molecules in the microemulsions in the presence of reagent beads, wherein the reagent beads are bound to a plurality of molecules of a primer for amplifying the analyte DNA molecules, whereby product beads are formed which are bound to a plurality of copies of the single species of analyte DNA molecule;
separating the product beads from analyte DNA molecules which are not bound to product beads;
isolating product beads which are bound to a plurality of copies of the single species of analyte DNA molecule from product beads which are bound to a plurality of copies of a second species of analyte DNA molecule;
amplifying the second species of analyte DNA molecule from the isolated product beads.

12. The method of claim 11 wherein the analyte DNA molecules are in a sample selected from the group consisting of urine, blood, sputum, stool, tissue, and saliva, of a eukaryotic organism.

13. A method for analyzing nucleotide sequences, comprising:
forming microemulsions comprising more than one species of analyte DNA molecules, such that a plurality of aqueous compartments comprise a single species of analyte DNA molecule;
amplifying analyte DNA molecules in the microemulsions in the presence of reagent beads, wherein the reagent beads are bound to a plurality of molecules of a primer for amplifying the analyte DNA molecules, whereby product beads are formed which are bound to a plurality of copies of the single species of analyte DNA molecule;
separating the product beads from analyte DNA molecules which are not bound to product beads;
determining a sequence feature of the single species of analyte DNA molecule which is bound to the product beads by a technique selected from the group consisting of: hybridization to a fluorescently labeled oligonucleotide probe; allele specific priming; single nucleotide extension; hybridization to a fluorescein-conjugated oligonucleotide probe; and hybridization to a biotin-conjugated oligonucleotide probe.

14. The method of claim 13 wherein the analyte DNA molecules are in a sample selected from the group consisting of urine, blood, sputum, stool, tissue, and saliva, of a eukaryotic organism.

15. The method of claim 13 wherein the technique used for determining is hybridization to a fluorescently labeled oligonucleotide probe.

16. The method of claim 15 wherein the oligonucleotide probe has a stem and loop structure.

17. The method of claim 13 wherein the technique used for determining is allele specific priming.

18. The method of claim 13 wherein the technique used for determining is single nucleotide extension.

19. The method of claim 13 wherein the technique used for determining is hybridization to a fluorescein-conjugated oligonucleotide probe.

20. The method of claim 19 wherein the oligonucleotide probe has a stem and loop structure.

21. The method of claim 13 wherein the technique used for determining is hybridization to a biotin-conjugated oligonucleotide probe.

* * * * *